United States Patent
Wachman et al.

[11] Patent Number: 5,407,949
[45] Date of Patent: Apr. 18, 1995

[54] STERILANT COMPOSITION

[75] Inventors: Stanley L. Wachman, Cherry Hill; Sidney Karlan, Nutley, both of N.J.

[73] Assignee: Cetylite Industries, Inc., Pennsauken, N.J.

[21] Appl. No.: 216,676

[22] Filed: Mar. 23, 1994

Related U.S. Application Data

[60] Division of Ser. No. 164,627, Dec. 9, 1993, Pat. No. 5,338,748, which is a continuation of Ser. No. 866,010, Apr. 9, 1992, abandoned, which is a continuation of Ser. No. 758,400, Aug. 27, 1991, Pat. No. 5,124,359, which is a continuation-in-part of Ser. No. 210,626, Jun. 23, 1988, Pat. No. 4,923,899, which is a continuation-in-part of Ser. No. 139,166, Dec. 22, 1987, abandoned, which is a continuation of Ser. No. 906,557, Sep. 8, 1986, abandoned, which is a continuation of Ser. No. 776,479, Sep. 16, 1985, abandoned, which is a continuation-in-part of Ser. No. 692,776, Jan. 18, 1985, abandoned.

[51] Int. Cl.⁶ ............... A01N 35/00; A01N 43/40; A01N 43/42; A01N 43/54
[52] U.S. Cl. .................... 514/358; 514/259; 514/307; 514/311; 514/334; 514/356; 514/705
[58] Field of Search ............... 514/358, 259, 307, 311, 514/356, 205, 334

[56] References Cited

U.S. PATENT DOCUMENTS

| | | | |
|---|---|---|---|
| 3,016,328 | 11/1962 | Pepper et al. | 424/127 |
| 3,282,775 | 11/1966 | Stonehill | 514/705 |
| 4,103,001 | 7/1978 | Schattner | 424/148 |
| 4,107,312 | 8/1978 | Wegner et al. | 514/642 |
| 4,320,147 | 3/1982 | Schaeufele | 514/643 |
| 4,444,785 | 4/1984 | Mandt et al. | 514/496 |

Primary Examiner—Allen J. Robinson
Attorney, Agent, or Firm—Lackenbach Siegel Marzullo Aronson & Greenspan

[57] ABSTRACT

A biocidal, aqueous composition for killing bacteria, spores, fungi, and viruses on nonabsorbent surfaces comprises at least one quaternary ammonium compound, at least one aliphatic dialdehyde having from two to six carbon atoms, and at least one aliphatic hydroxyl compound having form one to eight carbon atoms.

This sterilant is stable for weeks, is especially useful between pH 4 to 9, and may additionally comprise a chelating agent.

12 Claims, No Drawings

STERILANT COMPOSITION

RELATED U.S. APPLICATIONS

This is a divisional application of Ser. No. 08/164,627, filed Dec. 9, 1993, issued as U.S. Pat. No. 5,338,748 on Aug. 16, 1994, which is a continuation of application Ser. No. 07/866,010, filed Apr. 9, 1992, now abandoned, which is a continuation of application Ser. No. 758,400, filed Aug. 27, 1991, which has matured into U.S. Pat. No. 5,124,359, granted Jun. 23, 1992 which is a continuation-in-part of Ser. No. 210,626 filed Jun. 23, 1988 which has matured into U.S. Pat. No. 4,923,899, granted May 8, 1990, which is a continuation-in-part of Ser. No. 139,166 filed Dec. 22, 1987 now abandoned which is a continuation of Ser. No. 906,557 filed Sep. 8, 1986 now abandoned which is a continuation of Ser. No. 776,479 filed Sep. 16, 1985 now abandoned which is a continuation-in-part of Ser. No. 692,776 filed Jan. 18, 1985 now abandoned.

FIELD OF THE INVENTION

This invention relates to a broad-spectrum biocidal composition effective for the rapid killing of a wide variety of bacteria, spores, fungi, and viruses on a wide variety of nonabsorbent surfaces such as metals, plastics, resins, woods, rubbers, ceramics, and glasses. The composition of the present invention kills so many organisms on such a wide variety of surfaces that it may be termed a sterilant.

Some of the articles which may be sterilized by the composition of the present invention are counters, floors, sheets, catheters, dialysis machine tubing, anesthetic breathing bags, surgical instruments, dental bite blocks, saliva-draining tubes, respirator equipment, and environmental surfaces in general.

BACKGROUND OF THE INVENTION

In the past in medical and dental circles, steam sterilization or treatment with ethylene oxide in a closed apparatus have been considered ideal ways of sterilizing equipment. But for many types or parts of apparatus, steam sterilization is impractical because of the size or number of items to be sterilized. For parts of equipment which actually come in contact with the patient, such as dental bite blocks, anesthetic breathing bags, respirators, etc. it is impermissible for ethylene oxide to be used because residual trace amounts might harm the patient.

Hence, a stable, benign, broad-spectrum sterilant effective at a wide range of pH's is greatly desired by the medical/dental profession for environmental use, especially on nonabsorbent surfaces.

A disinfectant is generally considered to be an agent which destroys bacterial organisms which are growing, but not bacterial spores. Germicide and bactericide are approximately synonymous with disinfectant. An antiseptic inhibits the growth of microorganisms. A sporicide kills spores of fungi molds, and bacteria. Since spores are more resistant than bacteria, sporicides are generally considered sterilizing agents. Biocides kill all living microorganisms, hence also are sterilizing agents. A virucide kills viruses; a fungicide kills fungi. The novel sterilant of this invention kills bacteria, spores, fungi and viruses. Hence, it may be termed a biocide or a sterilant.

The Hamilton U.S. Pat. No. 3,208,936, discloses combining a broad range of quaternary amines as germicides and foaming agents in recirculation type toilets.

The Halley U.S. Pat. No. 3,785,971, is directed to a waste treatment material for a storage holding tank in which paraformaldehyde and an alkali carbonate or hydroxide are combined.

U.S. Pat. No. 2,998,390, granted August 29, 1961 to Hamilton and U.S. Pat. No. 3,107,216, granted Oct. 15, 1963 to Hamilton, disclose a recirculating toilet fluid which contains a quaternary ammonium salt.

"Quaternary Ammonium Salts as Germicidals. Nonacylated Quaternary Ammonium Salts Derived from Aliphatic Amines," Shelton, R. S. et al., *Journal of the American Chemical Society*, vol. 68, pp. 753–55 (1946), reported that alkyl quaternary ammonium salts have germicidal powers and N-benzyl substitutes do not affect this germical activity.

It was reported in Gardner, J. *Disinfection, Sterilization & Preservation*, p. 900, S. S. Block, ed., Lea & Febiger, 2nd ed. (1977) to include chelating agents with phenols and certain quaternary ammonium salts for enhanced activity against Gram-negative bacteria.

The Schattner U.S. Pat. No. 4,103,001 discloses an aqueous mixture of phenol, sodium tetraborate, and sodium phenate solution to which is added aqueous glutaraldehyde in order to kill some bacteria and bacterial spores. This mixture cannot be used against fungi or viruses.

The Stonehill U.S. Pat. No. 3,282,775 discloses a mixture of dialdehydes and a cationic surface active agent, plus a lower alcohol, which kills four spore-forming bacteria, but not fungi or viruses.

The Pepper U.S. Pat. No. 3,016,328 discloses that simple dialdehydes plus a lower alkanol to the extent of about 60 to 70% and an alkalinizing agent to yield a pH range of about 8 to 9.5 kill four spore-forming bacteria, two of which are the same as in U.S. Pat. No. 3,282,775.

Borick, et al in the Journal of Pharmaceutical Sciences, Vol. 53, No. 10 at p. 1273 disclose that glutaraldehyde alkalinized with sodium bicarbonate kills eight nonspore-forming bacteria, four spore-forming bacteria, one fungus, and nine viruses, but that this alkaline solution was stable only for about two weeks.

French Patent 2,321,300 discloses that a mixture of aldehyde and quaternary ammonium compound has antiseptic properties by reducing the growth of five bacteria of interest to the food industry.

British Patent 1,443,786 discloses that a mixture of glutaraldehyde, a lower alcohol, and a highly ionizable salt at acidic pH ranges kills four sporulating bacteria by ion-exchange with the calcium in the walls of the bacterial spores.

The Wagner U.S. Pat. No. 4,107,312 discloses a disinfectant mixture of a strong formaldehyde solution, plus minor amounts of glyoxal and glutaraldehyde, plus a quaternary ammonium salt, methanol to stabilize the formaldehyde, a nonionic wetting agent, optionally some alcohol or glycol, and a scent, all at a neutral pH in order to avoid corrosion of aluminum toilets (or minimize corrosion of magnesium toilets) in aircraft.

The Mandt U.S. Pat. No. 4,444,785 discloses a disinfecting solution for soft contact lenses against two nonsporulating bacteria comprising a very low concentration of 1,5 pentanedial at neutral pH compatible with the human eye.

The Schaeufele U.S. Pat. No. 4,320,147 discloses a germicidal composition comprising quaternary ammonium chlorides, plus builder salts, which are useful for disinfection against bacteria.

Canadian Patent No. 1,154,555 discloses a bactericide composition containing formaldehyde, glutaraldehyde and a quaternary ammonium ingredient.

French Patent No. 2,145,444 discloses a bactericide composition containing formaldehyde and a quaternary ammonium compound.

The Lockwood U.S. Pat. No. 3,505,690 relates to a disinfectant dispersing system.

The Buchalter U.S. Pat. No. 3,983,252 discloses a chemical disinfecting composition comprising a dialdehyde and an alkali metal salt of a hydrocarbon carboxylic acid and optionally an alcohol.

The Goldhaft U.S. Pat. No. 4,022,911 discloses a disinfectant composition comprising three essential active ingredients, namely a dimethyl quaternary ammonium halide salt, a phenol or derivative thereof, and formaldehyde.

Oshchepkova and Kochkin in the Proceedings of the First All-Union Conference on Biocorrosion, Biodamage, and Marine Encrustation (1975), C.A.91:69799p report that a mixture of organotin fumarates or acryloyloxy stannate mixed with N-alkyl pyridinium salts or tetraalkylammonium salts protect wood samples in water from two common bacteria—A.niger and P. purpureum.

OBJECTS OF THE INVENTION

It is an object of this invention to provide a stable, benign, nonodorous, solution which kills a broad-spectrum of bacteria, spores, fungi, and viruses rapidly at a wide range of pH.

It is a further object of this invention to provide a broad-spectrum sterilant which will remain an active solution for at least several weeks.

It is yet another object of this invention to provide a sterilant which is effective on hard, nonabsorbent, "environmental" surfaces such as anesthetic breathing bags, dialysis tubing, respirators, dental bite blocks, saliva-draining tubes, and the like for which sterilization by steam or ethylene oxide is either impractical or physiologically disfavored.

It is an object of the present invention to provide a sterilant composition effective for killing rapidly individual microorganisms or a combination of several different kinds of microorganisms, such as bacteria, spores, fungi and/or viruses.

Another object of the invention is to provide a sterilant for a wide variety of hard surfaces such as metals, plastics, resins, rubbers, ceramics, and glasses.

Yet another object of the present invention is to provide a sterilant which is effective in the presence of high concentrations of blood, sputum, feces, urine, vomitus, and other animal exudates.

Other objects of the present invention will be apparent to those skilled in the art.

SUMMARY OF THE INVENTION

Surprisingly, a broad-spectrum sterilant capable of rapidly killing bacteria, sporulating bacteria, spores, fungi, and viruses can be achieved by combining in an aqueous solution an effective amount of at least one quaternary ammonium compound, at least one aliphatic dialdehyde having from two to six carbon atoms, and at least one aliphatic hydroxyl compound having from one to eight carbon atoms.

Another aspect of the invention relates to the use of the novel sterilant on "hard" or "environmental" surfaces (nonabsorbing) such as medical or dental equipment for which previously steam sterilization or treatment with ethylene oxide were employed.

The sterilant of the present invention relates to a liquid composition which is effective for rapidly killing at least one microorganism or any combination of two or more different microorganisms such as bacteria, spores, fungi and viruses.

For still another aspect of the invention, the novel sterilant is employed over a wide range of pH and is stable for several weeks after having been compounded.

Yet another aspect of the present invention arises from its efficacy in the presence of high concentrations of blood, sputum, urine, feces, vomitus or other bodily liquids or suspensions.

A further aspect of the present invention is its efficacy in sterilizing hard surfaces of metals, plastics, rubbers, resins, wood, ceramics, or glasses.

A typical embodiment of the invention comprises:

| Component | Weight % |
|---|---|
| Alkylbenzyldimethylammonium chloride | 0.1 |
| Cetyldimethylethylammonium bromide | 0.1 |
| Glutaraldehyde | 2.6 |
| Isopropyl alcohol | 0.2 |
| Propylene glycol | 0.16 |
| Sodium nitrite | 0.11 |
| Tetrasodium ethylenediamine tetraacetate | 0.015 |
| Water | balance |

Processes for employing these sterilant compositions are also disclosed herein.

DETAILED DESCRIPTION OF THE INVENTION

As discussed above, the prior art discloses individual compounds or mixtures of compounds which kill or inhibit the growth of a narrow range of organisms such as some bacteria, spores, fungi, or viruses. The synergistic combination of the seven components of the present invention unexpectedly kills all types of the names organisms, hence it is a sterilant. Among the classes of organisms killed by the composition of the present invention alone or admixed together are Gram-negative bacteria, Gram-positive bacteria, algae, protozoa, Gram-positive spore-forming bacteria, fungi, and many types of viruses.

Among the many typos of viruses killed by the composition of the present invention are:
orbiviruses, orthomyxoviruses, papovaviruses, paramyxoviruses, parvoviruses, picornaviruses, poxviruses, coronaviruses, flaviviruses, herpesviruses, adenoviruses, arenaviruses, bynyaviridae, caliciviruses, reoviruses, retioviruses, rhabdoviruses, rotaviruses, togaviruses, and various unclassified viruses, plus plant viruses.

In addition to the bacteria, spores, protozoa, algae, fungi, and viruses categorized above, the composition of the present invention can kill alone or in combination with the other organisms typified above various miscellaneous organisms from the *Chlamydia Coxiella, Ehrlichia, Rickettsia, Rochalimaea, Wolbachia*, and Thai tick typhus.

It is to be emphasized that the composition of the present invention is a sterilant which can kill any or all of the types of organisms described here alone or in any combination.

At the end of the Examples of this specification and before the claims, several hundred representative specific organisms are listed in Tables I to VII on which the synergistic composition of the present invention is effective.

The cationic, quaternary salts useful in the present invention may contain either or both of aliphatic and aromatic moieties. Although quaternary ammonium salts are preferred, cationic phosphonium, or sulfonium, or any other positive nonmetallic nuclei may be selected. Some of the aliphatic or alicyclic substituents for the quaternary ions are alkyl groups containing one to 30 carbon atoms both linear and branched, alkoxy groups also containing one to 30 carbon atoms both linear and branched, alicyclic groups such as cyclohexyl and its alkylated or alkyloxylated derivatives, and halogenated alkyl, halogenated alicyclic, or halogenated alkyloxy derivatives.

Aromatic moieties, which may themselves be substituted by aliphatic, alicyclic, alkyloxy groups, useful as substituents for the quaternary cationic salts of the present invention are benzyl, tolyl, xylyl, naphthyl, pyridyl, benzal, quinolyl and the like.

More specifically, some aliphatic quaternary ammonium salts which are useful in the present invention are: tetramethyl ammonium halide, trimethylethyl ammonium halide, dimethyldiethyl ammonium halide, methyltriethyl ammonium halide, tetraethyl ammonium halide, cetyldimethylethyl ammonium halide, trimethyln-propyl ammonium halide, dimethyldin-propyl ammonium halide, methyltrin-propyl ammonium halide, tetran-propyl ammonium halide, methylethyln-propyln-butyl ammonium halide, ethyln-propyln-pentyl ammonium halide, trimethylallyl ammonium halide, dimethyldiallyl ammonium halide, methyltriallyl ammonium halide, tetraallyl ammonium halide, N,N,N,N',N',N'-hexaethyl-1,2-ethylene diammoniumhalide, N,N,N,N',N',N'-hexaethyl-1,4-butylene-diammonium halide, N,N,N'-dibenzyl-N,N,N',N', tetramethyl-1,2-ethylene diammonium halide, N,N'-di(4-chlorobenzyl)-N,N,N',N'-tetramethyl-1,2-ethylene diammonium halide, N,N,N'-tetraethyl-N,n''-dioctadecyl-1,2-ethylene diammonium halide, N,N,N',N'-tetraethyl-N,N'-dihexadecyl-1,4-butylene diammonium halide, octadecyltrimethyl ammonium halide, dioctadecyldimethyl ammonium halide, trioctadecylmethyl ammonium halide tetraoctadecyl ammonium halide, hexadecyltriethyl ammonium halide, hexadecyldimethylethyl ammonium halide, hexadecyldiethylmethyl ammonium halide, didecyldioctyl ammonium halide, didecyldihexyl ammonium halide, and hexyloctyldecyldodecyl ammonium halide.

Some representative useful quaternary ammonium salts containing an aromatic moiety include:
benzylodecyldimethyl ammonium halide, o-tolyldodecyldimethyl ammonium halide, m-tolyldodecyldimethyl ammonium halide, p-tolyldodecyldimethyl ammonium halide, 2,3-xylyldodecyldimethyl ammonium halide, 2,4-xylydodecyldimethyl ammonium halide, 2,5-xylyldodecyldimethyl ammonium halide, 3,4-xylyldodecyldimethyl ammonium halide, 3,5-xylyldodecyldimethyl ammoniuim halide, 2-chlorobenzyldodecyldimethyl ammonium halide, 3-chlorobenzyldodecyldimethyl ammonium halide, 4-chlorobenzyldodecyldimethyl ammonium halide, 2,3-dichlorobenzyldodecyldimethyl ammonium halide, 2,4-dichlorobenzyldodecyldimethyl ammonium halide, 2,5-dichlorobenzyldodecyldimethyl ammonium halide, 2,6-dichlorobenzyldodecyldimethyl ammonium halide, 3,4-dichlorobenzyldodecyldimethyl ammonium halide, 3,5-dichlorobenzyldodecyldimethyl ammonium halide, 2-nitrobenzyldodecyldimethyl ammonium halide, 3-nitrobenzyldodecyldimethyl ammonium halide, 4-nitrobenzyldodecyldimethyl ammonium halide, 2,4-dinitrobenzyldodecyldimethyl ammonium halide, 3,5-dinitrobenzyldodecyldimethyl ammonium halide, 2-sulfobenzyldodecyldimethyl ammonium halide, 3-sulfobenzyldodecyldimethyl ammonium halide, 4-sulfobenzyldodecyldimethyl ammonium halide, 2-carboxybenzyldodecyldimethyl ammonium halide, 3-carboxybenzyldodecyldimethyl ammonium halide, 4-carboxybenzyldodecyldimethYl ammonium halide, benzylhexyldimethyl ammonium halide, benzyloctyldimethyl ammonium halide, benzyldecyldimethyl ammonium halide, benzyldodecyldimethyl ammonium halide, benzyltetradecyldimethyl ammonium halide, benzylhexadecyldimethyl ammonium halide, benzyloctadecyldimethyl ammonium halide.

Some representative, useful quaternary ammonium salts containing heterocyclic, aromatic moieties include: n-hexylpyridinium halide, n-octylpyridinium halide, n-decylpyridinium halide, n-dodecylpyridinium halide, n-tetradecylpyridinium halide, n-hexadecylpyridinium halide, n-hexyllutidinium halide, n-octyllutidinium halide, n-decyllutidinium halide, n-dodecyllutidinium halide, n-tetradecyllutidinium halide, n-hexadecyllutidinium halide, n-hexylpicolinium halide, n-octylpicolinium halide, n-decylpicolinium halide, n-dodecylpicolinium halide, n-tetradecylpicolinium halide, n-hexadecylpicolinium halide, n-hexylquinolinium halide, n-octylquinolinium halide, n-decylquinolinium halide, n-dodecylquinolinium halide, n-tetradecylquinolinium halide, n-hexadecylquinolinium halide, n-hexylisoquinolinium halide, n-octylisoquinolinium halide, n-decylisoquinolinium halide, n-dodecylisoquinolinium halide, n-tetradecylisoquinolinium halide, n-hexadecylisoquinolinium halide, n-hexylquinazolinium halide, n-octylquinazolinium halide, n-decylquinazolinium halide, n-dodecylquinazolinium halide, n-tetradecylquinazolinium halide, n-hexadecylquinazolinium halide, n-hexylquinoxalinium halide, n-octylquinoxalinium halide, n-decylquinoxalinium halide, n-dodecylquinoxalinium halide, n-tetradecylquinoxalinium halide, n-hexadecylquinoxalinium halide, n-hexylpyridopyridinium halide, n-octylpyridopyridinium halide, n-decylpyridopyridinium halide, n-dodecylpyridopyridinium halide, n-tetradecylpyridopyridininum halide, and n-hexadecylpyridopyridinium halide.

The preferred counter ions for the quaternary cationic salts are halides, especially chloride and bromide. Particularly useful for practicing the present invention are alkylbenzyldimethyl ammonium chlorides, wherein the alkyl groups contain between 10 and 18 carbon atoms, and cetyldimethylethyl ammonium bromide. The useful range of quaternary cationic salts in an effective amount of sterilant is from about 0 05% to 3% in actual use by weight.

Other counter ions, anions, useful in the practice of the present invention to neutralize the positive charge of the ammonium, phosphonium, sulfonium, or other positive moieties can be found in the following list bicarbonate, bisulfite, fluoride, borate, carbonate, nitrite, nitrate, phosphite, phosphate, sulfite, sulfate, chloride, hypochlorite, chlorite, chlorate, perchlorate, hydroxide, fluoborate, iodide, iodate, periodate, and bromate.

The solubility of the various solutes in the novel sterilant of the instant invention is improved by using small amounts of alkanols having from one to six carbon atoms and/or glycols having from two to four carbon atoms. These alkanols and glycols also have concomitant and peripheral biocidal effect. Especially useful alkanols are methanol, ethanol, and isopropyl alcohol. Especially useful polyols are glycols such as ethylene glycol, propylene glycol, diethylene glycol, as well as glycerine. In the diluted solution for actual use, the effective amount for the alkanol is from about 0.1% to 3% by weight, and the effective amount for the polyol or glycol is from about 0.1% to 3% by weight.

Other alcohols having eight or less carbon atoms useful in the practice of the present invention are: 1-propanol, 1-butanol, 2-butanol, 2-methyl-1-propanol, 2-methyl-2-propanol, 1-pentanol, 2-pentanol, 3-pentanol, 2-methyl-2-butanol, 2-methyl-3-butanol, 2-methyl-4-butanol, 2,2-dimethyl-1-propanol, 1-hexanol, 2-hexanol, 3-hexanol, 2,2-dimethyl-3-butanol, 2,2-dimethyl-4-butanol, 2,3-dimethyl-2-butanol, 2-methyl-1-pentanol, 2-methyl-2-pentanol, 2-methyl-3-pentanol, 2-methyl-4-pentanol, 2-methyl-5-pentanol, 3-methyl-1-pentanol, 3-methyl-2-pentanol, 3-methyl-3-pentanol, 2,2-diethyl-1-ethanol, 1-heptanol, 2-heptanol, 3-heptanol, 4-heptanol, 2,2,3-trimethyl-3-butanol, 2,3-dimethyl-3-pentanol, 2,4-dimethyl-3-pentanol, 3-ethyl-1-pentanol, 3-ethyl-2-pentanol, 3-ethyl-3-pentanol, 4-ethyl-1-pentanol, 4-ethyl-2-pentanol, 4-ethyl-3-pentanol, 2-ethyl-1-pentanol, 2-methyl-1-hexanol, 2-methyl-2-hexanol, 2-methyl-3-hexanol, 2-methyl-4-hexanol, 3-methyl-1-hexanol, 4-methyl-1-hexanol, 5-methyl-1-hexanol, 3-methyl-2-hexanol, 4-methyl-2-hexanol, 3-methyl-3-hexanol, 3-methyl-4-hexanol, 1-octanol, 2-octanol, 3-octanol, 4-octanol, 2-methyl-1-heptanol, 3-methyl-1-heptanol, 4-methyl-1-heptanol, 5-methyl-1-heptanol, 5-methyl-1-heptanol, 6-methyl-1-heptanol, 2-methyl-2-heptanol, 3-methyl-2-heptanol, 4-methyl-2-heptanol, 5-methyl-2-heptanol, 6-methyl-2-heptanol, 2-methyl-3-heptanol, 3-methyl-3-heptanol, 4-methyl-3-heptanol, 5-methyl-3-heptanol, 6-methyl-3-heptanol, 2-methyl-4-heptanol, 3-methyl-4-heptanol, 4-methyl-4-heptanol, 5-methyl-4-heptanol, 6-methyl-4-heptanol, 2,2-dimethyl-1-hexanol, 3,3-dimethyl-1-hexanol, 4,4-dimethyl-1-hexanol, 5,5-dimethyl-1-hexanol, 2,3-dimethyl-1-hexanol, 2,4-dimethyl-1-hexanol, 2,5-dimethyl-1-hexanol, 3,4-dimethyl-1-hexanol, 3,5-dimethyl-1-hexanol, 2-ethyl-1-hexanol, 3-ethyl-1-hexanol, 4-ethyl-1-hexanol, and 5-ethyl-1-hexanol.

Other glycols having eight or less carbon atoms useful in the practice of the present invention are:
1,2-propanediol, 1,2-butanediol, 1,3-butanediol, 1,4-butanediol, 2-methyl-1,2-propanediol, 2,methyl-1,3-propanediol, 1,2-pentanediol, 1,3-pentanediol, 1,4-pentanediol, 1,5-pentanediol, 2-methyl-1,2-butanediol, 2-methyl-1,3-butanediol, 2-methyl-1,4-butanediol, 2-methyl-2,3-butanediol, 2-methyl-3,4-butanediol, 1,2-hexanediol, 1,3-hexanediol, 1,4-hexanediol, 1,5-hexanediol, 1,6hexanediol, 2-methyl-1,2-pentanediol, 2-methyl-1,3-pentanediol, 2-methyl-1,4-pentanediol, 2-methyl-1,5-pentanediol, 2-methyl-2,3-pentanediol, 2-methyl-2,3-pentanediol, 2-methyl-2,4-pentanediol, 2-methyl-2,5-pentanediol, 2-methyl-3,4-pentanediol, 2-methyl-3,5-pentanediol, 2-methyl-4,5-pentanediol, 2,3-dimethyl-1,2-butanediol, 2,3-dimethyl-1,3-butanediol, 2,3-dimethyl-1,4-butanediol, 2,3-dimethyl-2,3-butanediol.

Certain salts with anions at less than full oxidation state, such as nitrite, bisulfite, or chlorite, may be optionally employed in the novel sterilant solution of the instant invention to prevent corrosion, as well as for their biocidal activity.

Also useful in the practice of the present invention are cations wherein the metal oxidation state is lower than its chemically possible maximum.

Some useful compounds with less than full oxidation states are found in the following salts first some with reduced anions and then some salts with less oxidized cations, as follows: sodium phosphite, sodium sulfite, sodium hypochlorite, sodium chlorite, sodium chlorate, sodium selenite, sodium arsenite, sodium hypobromite, sodium bromite, sodium bromate, sodium stannite, sodium antimonite, sodium tellurite, sodium ferrocyanide, sodium manganite, sodium manganate, potassium phosphite, potassium, sulfite, potassium hypochorite, potassium chlorite, potassium chlorate, potassium selenite, potassium arsenite, potassium hypobromite, potassium bromite, potassium bromate, potassium stannite, potassium antimonite, potassium tellurite, potassium ferrocyanide, potassium manganite, potassium manganate, lithium phosphite, lithium sulfite, lithium hypochlorite, lithium chlorite, lithium chlorate, lithium selenite, lithium arsenite, lithium hypobromite, lithium bromite, lithium bromate, lithium stannite, lithium antimonite, lithium antimonite, lithium tellurite, lithium ferrocyanide, lithium manganite, lithium manganate, rubidium nitrite, rubidium phosphate, rubidium sulfite, rubidium hypochlorite, rubidium chlorite, rubidium chlorate, rubidium selenite, rubidium arsenite, rubidium hypobromite, rubidium bromite, rubidium bromate, rubidium stannite, rubidium antimonite, rubidium tellurite, rubidium ferrocyanide, rubidium manganite, rubidium manganate, cesium nitrite, cesium phosphite, cesium sulfite, cesium hypochlorite, cesium chlorite, cesium chlorate, cesium selenite, cesium arsenite, cesium hypobromite, cesium bromite, cesium bromate, cesium stannite, cesium antimonite, cesium telurite, cessium ferrocyanide, cesium manganite, cesium manganate, ferrous ferrocyanide, ferrous ferricyanide, cuprous chloride, ferrous phosphate, stannous chloride, ferrous sulfate, manganous sulfate, plumbous sulfate, and chromous chloride.

Particularly useful are sodium, potassium, lithium, and ammonium salts of nitrite, bisulfite, and chlorite; especially useful is sodium nitrite. These optional salts may be employed in the range from 0.05% to about 2.0% by weight of the actual solution employed.

A chelating agent may be optionally employed in the broad-spectrum sterilant of the present invention from 0% to 0.025% by weight to aid in solubility of the other components, to counteract any deleterious effects from diluting concentrated commercial strengths with hard water for use, and to help break down the coatings of spores, which have a high concentration of multivalent ions. The preferred chelating agent to practice the current invention may range from 0% to 0.025% by weight and is ethylene diamine tetraacetic acid (EDTA). Partial esters or salts of EDTA may also be used. An example of a salt of EDTA is tetrasodium ethylenediamine tetraacetate.

Other useful chelating agents may be found in the following acids, full salts, or partial salts of: oxalic acid, malonic acid, oxaldihydrixamic acid, diaminoglyoxime, dithiomalonic acid, glyoxime, maleic acid, fumaric acid, oxalacetic acid, diglycolic acid, tartaric acid, oxalenediuramidoxime, thiodiglycolic acid, iminodiacetic acid, nitrilotriacetic acid, dimethylglyoxime, hydrazine-N,N'-diacetic acid, citraconic acid, itaconic acid, 2,4-pentanedione, glutaric acid, N-methyliminodi-acetic acid, glutamic acid, aconitric acid (trans), gluconic acid, 1,2-cyclohexanediamine-N,N,N'-tetraacetic acid (cis&-trans), 1,2-ethylenediamine-N,N,N',N'-tetraacetic acid, N'-benzylethylene-diamine-N,N,N'-triacetic acid, diethylenetriamine-N,N,N',N",N"-pentaacetic acid, hexamethyldiamine-N,N,N',N'-tetraacetic acid, 2,2'''-ethylenedioxybis(ethyliminodiacetic acid), 2,2'-oxybis(propyliminodiacetic acid), triethylenetetraminehexaacetic acid, 1,3,5-triaminocyclohexanehexaacetic acid, and ethyl acetoacetate.

A dialdehyde containing up to six carbon atoms is a component of the broad-spectrum sterilant of the present invention. Dialdehydes include malonaldehyde, succinaldehyde, oxaldehyde (glyoxal), adipaldehyde, and preferably glutaraldehyde. Alternatively, these compounds may be termed aliphatic dials, e.g. 1,5 pentanedial. By themselves, these compounds are effective germicides to some degree, at high pH, but they fail to have the wide breadth and speed of killing of the mixture of the current invention. This is especially true for the killing of the sporulent bacteria, where the dialdehydes alone can take up to ten hours to kill spores, and for many viruses, where dialdehydes are ineffective. In the final dilution as used, in the present invention, an effective amount of the dialdehyde is from about 0.5% to about 7% by weight. A concentration of dialdehyde of about 2.6 to 5 weight % is preferred and a concentration of dialdehyde of 3.2 weight % is especially preferred.

Some useful dialdehydes in the practice of the present invention are the following compounds and their mixtures: 1,2-ethanedial, 1,3-propanedial, 1,4-butanedial, 1,5-pentanedial, 2-methyl-1,4-butanedial, 2-methyl-1,3-propanedial, 2,2-dimethyl-1,3-propanedial, 2,3-dimethyl-1,4-butanedial, 2,2-dimethyl-1,4butanedial, 1,6 hexanedial, 2-methyl-1,5-pentanedial, 3-methyl-1,5-pentanedial, 2-ethyl-1,3-propanedial, and 2-n-propylpropanedial, some examples of heterocyclic dialdehydes are furan-2,5-dialdehyde, furan-3,4-dialdehyde, thiophene-2,5-dialdehyde, thiophene-3,4-dialdehyde, pyrrole-2,5-dialdehyde, pyrrole-3,4-dialdehyde, imidazole-4,5-dialdehyde, pyrazole-3,4-dialdehyde, 1,2,3-triazole-4,5-dialdehyde, pyrazine-2,3-dialdehyde, pyrimidine-4,5-dialdehyde, pyridazine-3,4-dialdehyde, pyridazine-4,5-dialdehyde. Aliphatic dialdehydes are preferred, but heterocyclic dialdehydes such as those named above may also be employed.

As a practical matter, it is preferred to produce the broad-spectrum sterilant of the present invention in the form of one or more concentrated solutions prior to transport and storage. The concentrations of these solutions would be 50 to 100-fold higher strength than the actual use-strengths given above. After transport and storage, the user, normally a medical or dental technician, will dilute the concentrate to produce an effective amount at the ultimate dilution and then add the dialdehyde.

In concentrated form, a preferred embodiment of the sterilant concentrate of the present invention would have the following approximate concentrations by weight:

|  | Weight % |
| --- | --- |
| Alkyl*benzyldimethylammonium chloride | 7 |
| *50% C-12, 30% C-14, 17% C-16, 3% C-18 |  |
| Cetyldimethylethylammonium bromide | 7 |
| Isopropyl alcohol | 14 |
| Propylene glycol | 12 |
| Sodium nitrite | 7 |
| EDTA | 1.5 |
| Water, balance up to 100% |  |

In actual practice, the user will have prepared a desired quantity of the diluted sterilant concentrate by diluting the sterilant concentrate with distilled or tap water. This resulting solution will serve, further, as the diluent for the dialdehyde concentrate then to be added thereto.

The diluted sterilant solution after combination is an exceptionally broad-spectrum sterilant on a wide variety of metal, plastic, cross-linked resin, rubber, composite, coated, painted or natural wood, ceramic, or glass non-adsorbent surfaces, exemplified by but not limited to the following:

stainless steels (various), steels, not stainless (various), galvanized iron, copper, brass, aluminum, chromium plated metals, tinned plating metals, enameled metals, polyethylene, polypropylene, polystyrene, acrylics, polyacetals, nylons, "epoxy resin"-coated wood, polyurethane-coated wood, alkyd resin painted wood, alkyd resin-coated metal, oil-based painted wood, phenol-formaldehyde resin laminates ("Formica" type), polyvinyl chloride-based furniture surfaces ("Naugahyde" type), gum rubber surgical/dental adjuncts (dental dam, tubing, catheters, gloves), hard rubber devices (bite blocks), water-based, latex-painted wood, glazed porcelain and other ceramics and various types of glass such as lime, flint, and borosilicates.

The present invention will now be described by reference to the following examples, which are not to be deemed limitative of the present invention in any manner thereof.

EXAMPLE A

This example illustrates the preparation of an effective sterilizing amount of a final user solution of the sterilant composition of the invention.

A 15 ml ampule of the above sterilant concentrate was diluted with distiled water to a final volume of 1 liter. This was a dilution ratio of about 66.7:1. To this solution was added 50 ml of an aqueous 50% by weight solution of glutaraldehyde concentrate. On a weight basis, the concentration of glutaraldehyde will be about 2.6% in the final user solution.

Thus in the final user solution, the concentrations of the various components in the diluted sterilant will be as follows:

|  | Wt. % |
| --- | --- |
| Alkylbenzyldimethylammonium chloride | 0.1 |
| Cetyldimethylethylammonium bromide | 0.1 |
| Isopropyl alcohol | 0.2 |
| Propylene glycol | 0.16 |
| Sodium nitrite | 0.1 |
| EDTA | 0.02 |
| Dialdehyde, esp. glutaraldehyde | 2.6 |
| Water | balance |

The diluted sterilant composition of the present invention may be employed over a wide, useful pH range from about pH 4 to about pH 9. The preferred range for use is from about pH 5 to about pH 8. This is in marked contrast to the use of alkalinized dialdehydes alone, which are effective only from about pH 7 to about pH 8.5. Although buffers may optionally be employed to keep the sterilant of the instant invention within a narrow pH range, no buffer is necessary to practice this invention.

EXAMPLE B

This example illustrates the preparation of an effective sterilizing amount of a final user solution of the sterilant composition of the invention.

A 15 ml ampule of the above sterilant concentrate was diluted with distilled water .to a final volume of 750 ml. This was a dilution ratio of about 50:1. To this solution was added 50 ml of an aqueous 50% by weight solution of glutaraldehyde concentrate. On a weight basis, the concentration of glutaraldehyde will be about 3.2% in the final user solution.

Thus, in the final user solution, the concentrations of the various components in the diluted sterilant will be as follows:

|  | Wt. % |
|---|---|
| Alkylbenzyldimethylammonium chloride | 0.15 |
| Cetyldimethylethylammonium bromide | 0.15 |
| Isopropyl alcohol | 0.25 |
| Propylene glycol | 0.20 |
| Sodium nitrite | 0.15 |
| EDTA | 0.025 |
| Dialdehyde, esp. glutaraldehyde | 3.2 |
| Water | balance |

The diluted sterilant composition of the present invention may be employed over a wide, useful pH range from about pH 4 to about pH 9. The preferred range for use is from about pH 5 to about pH 8. This is in marked contrast to the use of alkalinized dialdehydes alone, which are effective only from about pH 7 to about pH 8.5. Although buffers may optionally be employed to keep the sterilant of the instant invention within a narrow pH range, no buffer is necessary to practice this invention.

EXAMPLE 1

This example illustrates the effectiveness of the sterilant composition of EXAMPLE A for nonsporulating bacteria.

The novel sterilant of the present invention was prepared with 400 ppm hard water as the diluent for test purposes:

|  | Wt. % |
|---|---|
| Alkylbenzyldimethylammonium chloride | 0.1 |
| Cetyldimethylethylammonium bromide | 0.1 |
| Isopropyl alcohol | 0.2 |
| Propylene glycol | 0.16 |
| Sodium nitrite | 0.11 |
| EDTA | 0.02 |
| Glutaraldehyde | 2.60 |
| Water | balance |

Employing the Use-Dilution Method of the Association of Official Agricultural Chemists (AOAC) 60 ring carriers were tested on three batchs each for efficacy against the following organisms (US EPA Procedure DIS/TSS-1 and 2 of January 1982); *Salmonella choleraesius* ATCC 10708 (Gram-negative), *Staphylococcus aureus* ATCC 6538 (Gram-positive), and *Pseudomonas aeruginosa* ATCC 15442 (Gram-positive, nosocomial pathogen).

All these microorganisms were killed within 10 minutes at 20 degrees C.

EXAMPLE 2

This example illustrates the efficacy of the broad-spectrum sterilant of the present invention for killing sporulating bacteria.

The novel sterilant solution was prepared as in EXAMPLE 1 for testing against Gram-positive, sporulating bacteria *Bacillus subtilus* ATCC 19659 and *Clostridium sporogenes* ATCC 3584 employing US EPA Procedure DIS/TSS-9 o f April 1981 (AOAC Sporicidal Test). Sixty carriers for each type of surface, porcelain penicylinders and silk suture loops, for each of three samples for each of three batches involved a total of 720 carriers.

As required, all microorganisms were killed on all carriers in about 5 hours, less than 6 hours at 20 degrees C.

In a similar test alkalinized glutaraldehyde can meet this standard only after 10 hours of contact.

EXAMPLE 3

This example illustrates the efficacy of the broad-spectrum sterilant of the present invention for killing fungi and fungal spores.

The novel sterilant solution was prepared as in EXAMPLE 1 for testing against pathogenic fungus *Trichophyton mentagrophytes* ATCC 27289 according to the AOAC Fungicidal Test by EPA procedure DIS/TSS-6 of August 1981. For this fungus two batches were used for two samples each killing all organisms within 10 minutes at 20 degrees C.

EXAMPLE 4

This example illustrates the efficacy of the broad-spectrum sterilant of the present invention in killing viruses, some of which none of the components of the novel sterilant can kill individually under the same conditions.

The novel sterilant solution was prepared as in EXAMPLE 1 for testing against the following viruses: *Herpes Simplex* I and II, Coxsackie virus B1, Coxsackie virus A9, Vaccinia Virus, Influenza virus A, Adenos virus II, Poliovirus I, Rhino virus, Cytomegalo virus, and Corona virus, all according to EPA procedure DIS/TSSD-7. For two batches each, four replicates were carried by ten-fold dilution and measured to three-log diminution. After incubation, the samples were recovered after adsorption time on mammalian cell monolayers.

The novel sterilant inactivated all the viruses within 10 minutes at 20 degrees C. It is known that alkalinized glutaraldehyde fails to inactivate at least Coxsackie virus and Poliovirus I under these conditions.

EXAMPLE 5

This example illustrates the effectiveness of the sterilant composition of EXAMPLE B for nonsporulating bacteria.

The novel sterilant of the present invention was prepared with 400 ppm hard water as the diluent for test purposes:

| | Wt. % |
|---|---|
| Alkylbenzyldimethylammonium chloride | 0.15 |
| Cetyldimethylethylammonium bromide | 0.15 |
| Isopropyl alcohol | 0.25 |
| Propylene glycol | 0.20 |
| Sodium nitrite | 0.15 |
| EDTA | 0.025 |
| Glutaraldehyde | 3.2 |
| Water | balance |

Employing the Use-Dilution Method of the Association of Official Agricultural Chemists (AOAC) 60 ring carriers were tested on three batchs each for efficacy against the following organisms (US EPA Procedure DIS/TSS-1 and 2 of January 1982); *Salmonella choleraesius* ATCC 10708 (Gram-negative), *Staphylococcus aureus* ATCC 6538 (Gram-positive), and *Pseudomonas aeruginosa* ATCC 15442 (Gram-positive, nosocomial pathogen).

All these microorganisms were killed within 10 minutes at 20 degrees C.

EXAMPLE 6

This example illustrates the efficacy of the broad-spectrum sterilant of the present invention for killing sporulating bacteria.

The novel sterilant solution was prepared as in EXAMPLE 5 for testing against Gram-positive, sporulating bacteria *Bacillus subtilus* ATCC 19659 and *Clostridium sporogenes* ATCC 3584 employing US EPA Procedure DIS/TSS-9 of April 1981 (AOAC Sporicidal Test). Sixty carriers for each type of surface, porcelain penicylinders and silk suture loops, for each of three samples for each of three batches involved a total of 720 carriers.

As required, all microorganisms were killed on all carriers in about 5 hours, less than 6 hours at 20 degrees C.

In a similar test alkalinized glutaraldehyde can meet this standard only after 10 hours of contact.

EXAMPLE 7

This example illustrates the efficacy of the broad-spectrum sterilant of the present invention for killing fungi and fungal spores.

The novel sterilant solution was prepared as in EXAMPLE 5 for testing against pathogenic fungus *Trichophyton mentagrophytes* ATCC 27289 according to the AOAC Fungicidal Test by EPA procedure DIS/TSS-6 of August 1981. For this fungus two batches were used for two samples each killing all organisms within 10 minutes at 20 degrees C.

EXAMPLE 8

This example illustrates the efficacy of the broad-spectrum sterilant of the present invention in killing viruses, some of which none of the components of the novel sterilant can kill individually under the same conditions.

The novel sterilant solution was prepared as in EXAMPLE 5 for testing against the following viruses: *Herpes Simplex* I and II, Coxsackie virus B1, Coxsackie virus A9, Vaccinia Virus, Influenza virus A, Adenos virus II, Poliovirus I, Rhino virus, Cytomegalo virus, and Corona virus, all according to EPA procedure DIS/TSSD-7. For two batches each, four replicates were carried by ten-fold dilution and measured to three-log diminution. After incubation, the samples were recovered after adsorption time on mammalian cell monolayers.

The novel sterilant inactivated all the viruses within 10 minutes at 20 degrees C. It is known that alkalinized glutaraldehyde fails to inactivate at least Coxsackie virus and Poliovirus I under these conditions.

The sterilant composition of the present invention has the advantages of being effective to kill a broad spectrum of microorganisms very rapidly with low concentrations of the active ingredients. The sterilant composition as a combination of ingredients is more effective against several microorganisms together at the same time than would be possible by using each active ingredient separately against the combination of microorganisms.

The sterilants of the disclosure above exemplified by the preferred embodiments of the various Examples are effective against a wide variety of microorganisms such as those of Tables I through VII.

TABLE I

| VIRUSES |
|---|
| ADENOVIRUSES |
| Avian adenovirus Types 1–10 |
| Marble spleen disease virus |
| Bovine adenovirus Types 1–8 |
| Canine adenovirus |
| Infectious canine hepatitis |
| Human adenovirus Types 1–41 |
| Mouse adenovirus |
| Swine adenovirus |
| Baboon adenovirus |
| Chimpanzee adenovirus |
| Simian adenovirus |
| Types 1–39 |
| ARENAVIRUSES |
| Amapari |
| Junin |
| Latino |
| Lymphocytic choriomeningitis |
| Bolivian Hemorrhagic Fever |
| Parana |
| Pichinde virus |
| Tacaribe virus |
| Tamiami virus |
| BUNYAVIRIDAE |
| Anopheles Group |
| Bunyamwera Super Group |
| Bwamba Group |
| California Group |
| Capim Group |
| Gamboa Group |
| Guama Group |
| Koongol Group |
| Patois Group |
| Simbu Group |
| Tete Group |
| Turlock Group |
| Phleboviruses |
| Nairoviruses |
| Hantaviruses |
| CALICIVIRUSES |
| Feline conjunctivitis |
| Feline picornavirus |
| Feline stomatitis |
| CORONAVIRUSES |
| Calf diarrheal coronavirus |
| Canine coronavirus |
| Feline infectious peritonitis |
| Hemagglutinating encephalomyelitis |

TABLE I-continued
VIRUSES

Human coronavirus
Infectious bronchitis
Mouse hepatitis virus
Rabbit coronavirus
Rat coronavirus
Sialodacryoadenitis virus
Transmissible
gastroenteritis
Turkey enteritis
coronavirus

FLAVIVIRUSES
Banzi
Bukalasa
Bussuquara
Cowbone ridge
Dakar bat
Dengue Types 1-4
Edge Hill
Entebbe bat
Ilheus
Japanese encephalitis
Kokobera
Kyasanur
Louping III
Modoc
Montana myotis
leukoencephalitis
Murray Valley encephalitis
Ntaya
Powassan
Rio Bravo
Russian spring-summer
encephalitis
Sepik
Simian hemorrhagic fever
St. Louis encephalitis
Stratford
Tenbusu
Uganda S
West Nile
Yellow fever
Zika

EERPESVIRUSES
Avian laryngotracheitis
Duck enteritis
Falcon herpesvirus
Lake Victoria cormorant
Marek's disease
Parrot herpesvirus
Pigeon herpesvirus
Turkey herpesvirus
Bovine herpesvirus
Infectious bovine
rhinotracheitis
Canine herpesvirus
Equine cytomegalovirus
Equine herpesvirus
Feline herpesvirus
Feline rhinotracheitis virus
Channel catfish
Herpesvirus salmonis
Guinea pig herpes-like virus
Guinea pig salivary gland
virus
Guinea pig X virus
Burkitt's lymphoma
Cytomegalovirus
Herpes simplex Types 1 & 2
Varicella
Varicella-Zoster
B Virus
Hepatitis A,B & C virus
Herpesvirus aotus
Herpesvirus ateles
Herpesvirus saguinus
Herpesvirus saimiri
Monkey cytomegalovirus
Simian herpesvirus 2 & 3
Squirrel monkey
cytomegalovirus

TABLE I-continued
VIRUSES

Pseudorabies
Caprine herpesvirus
Frog Virus 4
Mouse Salivary Gland Virus
Rabbit herpesvirus

ORBIVIRUSES
Bluetongue all types
Changuinola
Colorado tick fever
Corriparta
Epizootic hemorrhagic
disease of deer
Ieri
Irituia
Lebomba
Tribec
Wad Medani

ORTHOMYXOVIRUSES
Avian Influenza
Horse Influenza A
Human Influenza
A, B & C
Swine Influenza
Thogoto

PAPOVAVIRUSES
Human polyoma
Bovine papilloma
Human papilloma
JC virus
K-virus
Lymphotropic Papovavirus
Papilloma
Polyoma
Simian Papovavirus
SV-40

PARAMYXOVIRUSES
Bluegill
Bovine morbillivirus-like
Bovine respiratory
syncytial virus
Canine distemper
Canine parainfluenza
Fer de Lance virus
Measles
Mumps
Nariva
Newcastle disease
Parainfluenza
Pneumonia virus of mice
Respiratory syncytial
Simian paramyxovirus
Subacute sclerosing
panencephalitis
Yucaipa

PARVOVIRUSES
Adeno-associated virus
Aleutian disease
Avian adeno-associated
Bovine parvovirus
Canine parvovirus
Feline paneukopenia
Hemorrhagic encephalopathy
Porcine parvovirus

PICORNAVIRUSES
Poliovirus 1, 2 & 3
Coxsackievirus, all types
Echovirus, all types
Enterovirus, all types
Human rhinovirus, all types
Avian encephalomyelitis
Baboon enterovirus
Bovine enterovirus,
all types
Bovine rhinovirus,
all types
Encephalomyocarditis
Mouse encephalomyelitis
Porcine enterovirus,
all types TABLE I-continued
VIRUSES Rat encephalomyelitis
Simian picornavirus, all types
POXVIRUSES
Alastrim (Variola minor)
Bovine papular stomatitis
Canary pox
Cotia
Cowpox
Embu
Fibroma
Fowlpox
Milker's nodule virus
Monkeypox
Myxoma
Rabbit fibroma
Rabbitpox
Raccoonpox
Smallpox
Swine pox
Tanapox
Vaccinia
Yabu tumor poxvirus
REOVIRUSES
Avian reovirus, all types
Feline reovirus
Reovirus, all types
Turkey enteric reovirus
RETROVIRUSES
Avian leukosis-sarcoma complex
Avian reticuloendotheliosis group
Feline leukemia group
Murine leukemia-sarcoma group
Bovine syncytial virus
Caprine arthritis-encephalitis virus
Feline syncytia-forming
Human T-cell lukemia virus
Human immunodeficiency virus
Mouse mammary tumor
Simian foamyvirus
Squirrel monkey retrovirus
Syncytium-forming virus of Marmosets
Visna virus
RHABDOVIRUSES
Aruac
Bovine paralytic rabies
Chaco
Chandipura
Cocal virus
Hart virus
Infectious hematopoietic necrosis
Jurona
Kern Canyon
Klamath
Kwatta
Lagos bat
March
Mokola
Mossuril
Mount Elgon bat
Navorro
Piry virus
Rabies
Sawgrass
Timbo
Vesicular stomatitis
ROTAVIRUSES
Bovine rotavirus
Calf rotavirus
Human rotavirus
Porcine pararotavirus
Porcine rotavirus TABLE I-continued
VIRUSES Rhesus rotavirus
Simian rotavirus
TOGAVIRUSES
Alphavirus group
Pestiviruses
Rubeviruses
UNCLASSIFIED VIRUSES
Anaplasma marginale
Creutzfeldt-Jakob
Duck hepatitis
Eretmapodites
Equine infectious anemia virus
Frog virus 3
Golden shine virus
Grunt fin agent
Hepatitis A virus
Hepatitis B virus
Ichampadi
Infectious bursal disease of chickens
Infectious pancreatic necrosis of trout
Infectious pancreatic necrosis virus
Kuru
Lymphocystis
Matucare
Nodamura virus
Quaranfil
Tadpole edema virus
Tembe
Venkatapuram
Wanowrie
PLANT VIRUSES
Agropyron Mosaic
Alfalfa Mosaic
Apple Chlorotic
Apple Mosaic
Artichoke Latent
Barley Stripe Mosaic
Barley Yellow Dwarf
Bean Common Mosaic
Bean Golden Mosaic
Bean Pod Mottle
Bearded Iris Mosaic
Beet Curly Top
Beet Mosaic
Beet Western Yellows
Belladonna Mottle
Bidens Mottle
Broad Bean
Broccoli Necrotic
Carnation Mottle
Cherry Leaf Rool
Chrysanthemum Aspermy
Citrange Stunt
Cowpea Chlorotic Mottle
Desmodium Yellow Mottle
Elm Mosaic
Glycine Mottle
Grapevine Fanleaf
Henbane Mosaic
Lettuce Mosaic
Lychnis Ringspot
Maize rough Dwarf
Myrobalan Latent Ringspot
Nasturtium Ringspot
Oat Blue Dwarf
Onion Yellow Dwarf
Pangola Stunt
Panicum Mosaic
Passionfruit Woodiness
Peanut Stunt
Plantago Mottle
Poa Semilatent
Pokeweed Mosaic
Prunus Necrotic Ringspot
Raspberry Bushy Dwarf
Scophularia Mottle

TABLE I-continued
VIRUSES

Tobacco Mosaic
Tomato Aspermy
Tulip Breaking
Watermelon Mosaic
White Clover Mosaic
Wound Tumor

TABLE II
MISCELLANEOUS ORGANISMS

Chlamydia psittaci
Chlamydia trachomatis
Coxiella burneti
Ehrlichia risticii
Rickettsia akari
Rickettsia canada
Rickettsia conori
Rickettsia montana
Rickettsia mooseri
Rickettsia prowazeki
Rickettsia rickettsii
Rickettsia sennetsu
Rickettsia tsutsugamushi
Rochalimaea quintana
Rochalimaea vinsonii
Thai tick typhus
Wolbachia persica

TABLE III
GRAM NEGATIVE BACTERIA

| | |
|---|---|
| Acetobacter acet | Flavobacterium |
| Acholeplasma laidlawii | meningosepticum |
| Achromobacter viscosus | Francisella tularensis |
| Acidiphilium cryptum | Fusobacterium necrophorum |
| Acinetobacter calcoaceticus | Gardnerella vaginalis |
| Acinetobacter anatratus | Haemophilus aegyptius |
| Acinetobacter lwoffii | Hafnia alvei |
| Actinomyces bovis | Klegsiella oxytoca |
| Actinomyces israelii | Klebsiella pneumoniae |
| Actinomyces pyogenes | Legionella cherrii |
| Actinoplanes violaceus | Legionella feelei |
| Aeromonas hydrophila | Legionella pneumophila |
| Aeromonas salmonicida | Leptospira biflexa |
| Agrobacterium tumefaciens | Moraxella phenylpyruvica |
| Alcaligenes denitrificans | Morganella morganii |
| Alcaligenes faecalis | Mycoplasma canis |
| Anaerorhabdus furcosus | Mycoplasma hyorhinis |
| Aquaspirillum anulus | Mycoplasma pneumoniae |
| Arachnia propionica | Neisseria gonorrhoea |
| Arthrobacter ilicis | Neisseria meningitidis |
| Azotobacter beijerinckii | Oligella urethralis |
| Bacteroides bivius | Pasteurella multocida |
| Bacteroides fragilis | Proteus mirabilis |
| Bacteroides levii | Proteus vulgaris |
| Bdellovibrio solpii | Providencia rettgeri |
| Beggiatoa alba | Providencia rustigianii |
| Beijerinckia indica | Providencia stuartii |
| Bifidobacterium boum | Pseudomonas aeruginosa |
| Bordetella bronchiseptica | Pseudomonas avenae |
| Bordetella pertussis | Pseudomonas cepacia |
| Borrelia burgdorferi | Pseudomonas pseudomallei |
| Brucella abortus | Pseudomonas putida |
| Campylobacter coli | Salmonella choleraesuis |
| Campylobacter jejuni | Salmonella typhi |
| Campylobacter pylori | Salmonella typhimurium |
| Chlamydia psittaci | Serratia liquefaciens |
| Chlamydia trachomatis | Serratia marcescens |
| Chromobacterium violaceum | Shigella boydi |
| Citrobacter freundii | Shigella dysenteriae |
| Comamonas terrigena | Shigella flexneri |
| Deleya aesta | Shigella sonnei |
| Deleya venusta | Thiobacillus thiooxidans |
| Dermatophilus congolensis | Treponema hyodysenteriae |
| Edwardsiella tarda | Treponema pallidum |
| Eikenella corrodens | Ureaplasma gallorale |
| Enterobacter aerogenes | Veillonella caviae |
| Enterococcus avium | Vibrio cholerae |

TABLE III-continued
GRAM NEGATIVE BACTERIA

| | |
|---|---|
| Enterococcus faecalis | Wolinella succinogenes |
| Enterobacter cloacae | Xanthobacter flavus |
| Erwinia citreus | Xanthomonas campestris |
| Escherichia coli | Yersinia pestis |
| Ewingella americana | Zymomonas mobiles |

TABLE IV
GRAM POSITIVE BACTERIA

| | |
|---|---|
| Deinococcus erythromyxa | Mycobacterium bovis |
| Deinococcus proteolyticus | Mycobacterium fortuitum |
| Erysipelothrix insidiosa | Mycobacterium |
| Erysipelothrix rhusiopathiae | intracellulare |
| Eubacterium aerofaciens | Mycobacterium leprae |
| Eubacterium angustum | Mycobacterium tuberculosis |
| Eubacterium combesii | Norcardia asteroides |
| Eubacterium eligens | Norcardia brasiliensis |
| Eubacterium fossor | Paracoccus denitrificans |
| Jonesia denitrificans | Pediococcus dextrinicus |
| Kurthia gibsonii | Peptostreptococcus |
| Lactobacillus agilis | asaccharolyticus |
| Lactobacillus brevis | Peptostreptococcus micros |
| Lactobacillus buchneri | Phormidium sp |
| Lactobacillus carnis | Planococcus citreus |
| Lactobacillus casei | Propionibacterium acnes |
| Lactobacillus divergens | Propionibacterium |
| Lactobacillus helveticus | freudenreichii |
| Lactobacillus jensenii | Rhodococcus equi |
| Lactobacillus kefir | Rhodococcus erythropolis |
| Lactobacillus xylosis | Sarcina maxima |
| Lactococcus garviae | Stalphylococcus aureus |
| Lactococcus lactis | Staphylococcus epidermidis |
| Lactococcus plantarum | Staphylococcus hominis |
| Leptothrix buccalis | Staphylococcus warneri |
| Leuconostoc lactis | Stomatococcus |
| Leuconostoc mesenteroides | mucilaginosus |
| Leuconostoc oenos | Streptobacillus |
| Listeria grayi | moniliformis |
| Listeria innocua | Streptococcus dysgalactiae |
| Listeria monocytogenes | Streptococcus equi |
| Micrococcus agilis | Streptococcus equisimilus |
| Micrococcus cryophilus | Streptococcus faecalis |
| Micrococcus halobius | Streptococcus pyogenes |
| Micrococcus luteus | Streptomyces albulus |
| Mycobacerium aurum | Streptomyces vulgaris |
| Mycobacterium avium | |

TABLE V
GRAM POSITIVE SPORE FORMING BACTERIA

| Bacillus | Clostridium |
|---|---|
| acidocaldarius | acetobutylicum |
| alcalophilus | acidiurici |
| alvei | aerotolerans |
| aminoglucosidicus | barkeri |
| aneurinolyticus | beijerinickii |
| anthracis | bifermentans |
| badius | botulinum |
| brevis | cadaveris |
| capitovalis | carnis |
| cereus | cellulolyticum |
| chitinosporus | chauvoei |
| circulans | clostridiiforme |
| cirroflagellosus | coccoides |
| coagulans | collagenovorans |
| epiphytus | cylindrosporum |
| fastidiosus | difficile |
| filicolonicus | durum |
| firmus | flavum |
| freudenreichii | formicoaceticum |
| fructosus | haemolyticum |
| globigii | hastiforme |
| globisporus | histolyticum |
| gordonae | indolis |
| implexus | kaneboi |
| insolitus | kluyveri |
| laevolacticus | lentoputrescens |

TABLE V-continued
GRAM POSITIVE SPORE FORMING BACTERIA

| | |
|---|---|
| larvae | limosum |
| laterosporus | lortetii |
| lentimorbus | perfringens |
| lentus | putrificum |
| licheniformis | septicum |
| megaterium | sordellii |
| mycoides | sporogenes |
| pumilus | tetani |
| schlegelii | tetanomorphum |
| stearothermophilus | thermocellum |
| subtilis | thermolacticum |
| thuringiensis | tyrobutyricum |
| xerothermodurans | villosum |

TABLE VI
FUNGI

| | |
|---|---|
| Absidia blakesleeana | Entonaema liquescens |
| Achaetomium luteum | Epidermophyton floccosum |
| Achlya hypogyna | Filobasidiella neoformans |
| Aciculoconidium aculeatum | Fonsecaea pedrosoi |
| Acladium castellanii | Fusarium solani |
| Acemoniella lutzi | Geotrichum candidum |
| Acrodontium salmoneum | Gibberella baccata |
| Actinodendron verticillatum | Gymnosporangium globosum |
| Actinomucor elegans | Histoplasma capsulatum |
| Acytostelium elipticum | Kluyveromyces wickerhamii |
| Agaricus abruptibulbus | Madurella mycetomi |
| Agaricus campestris | Melampsora medusae |
| Akenomyces costatus | Microsporum canis |
| Alternaria alternata | Mucor hiemalis |
| Alternaria citri | Nectriella pironii |
| Armillaria limonea | Neurospora tetrasperma |
| Arthrobotrys oligospora | Paecilomyces lilacinus |
| Arthroderma benhamiae | Penicillium aurantiogriseum |
| Arthroderma gypseum | Phialophora richardsiae |
| Arthroderma incurvatum | Phycomyces nitens |
| Articulospora tetracladia | Pichia membranaefaciens |
| Aspergillus carneus | Pityrosporium ovale |
| Aspergillus fischeri | Pseudallescheria boydii |
| Aspergillus fumigatus | Puccinis graminis |
| Aspergillus niger | Pyrenophora trichostoma |
| Aureobasidium mansonii | Rhizoctonia repens |
| Basidiobolus haptosporus | Rhizomucor pusillus |
| Blastobotrys aristata | Rhizopus microsporus |
| Blastomyces dermatitidis | Rhodotorula rubra |
| Blastoschizomyces capitatus | Rhynchosporium secalis |
| Botrytis squamosa | Saccharomyces cerevisiae |
| Byssochlamys fulva | Sclerotium rolfsii |
| Candida albicans | Sporothrix schenckii |
| Candida tropicalis | Sporotrichum thermophile |
| Cephalosporium deformans | Stemphylium botryosum |
| Ceratocytis ulmi | Torula thermophila |
| Chaetomium globosum | Torulopsis pintolopesii |
| Chrysosporium pannorum | Trichoderma polysporum |
| Cladosporium carpophilum | Trichophyton mentagrophytes |
| Cladosporium resinae | Trichophyton rubrum |
| Coccidioides immitis | Ulocladium botrytis |
| Cronartium fusiforme | Uromyces phaseoli |
| Cryptococcus neoformans | Verticillium nigrescens |
| Curvularia prasadii | Xylohypha bantiana |
| Dictyostelium discoideum | Yarrowia lipolytica |
| | Zygosaccharomyces bailii |

TABLE VII
PROTISTS - ALGAE/PROTOZOA

| | |
|---|---|
| Acanthamoeba astronyxis | Leishmania hertigi |
| A. castellanii | Leishmania mexicana |
| A. culbertsoni | Leishmania tropica |
| A. hatchetti | Leptomonas pyrrhocoris |
| A. lenticulata | Lingulamoeba leei |
| A. polyphaga | Lohomonas piriformis |
| A. royreba | Monocercomonas colubrorum |
| Babesia microti | Muriella aurantiaca |
| Botrydium cystosum | Naegleria australiensis |
| Cephaleuros virescens | Naegleria fowleri |
| Chlamydomonas dorsoventralis | Naegleria gruberi |

TABLE VII-continued
PROTISTS - ALGAE/PROTOZOA

| | |
|---|---|
| Chlorella protothecoides | Naegleria jadini |
| Chlorella saccharophilia | Nosema necatrix |
| Chlorella sorokiniana | Ochromonas malhamensis |
| Chlorella variegata | Paramecium primaurelia |
| Chlorella xanthella | Paramecium multimicronucleatum |
| Chlorella zopfingiensis | |
| Chlorogonium elongatum | Pentatrichoimonas hominis |
| Crithidia fasciculata | Plasmodium brasilianum |
| Dientamoeba fragilis | Plasmodium coatneyi |
| Dunaliella tertiolecta | Plasmodium cynomolgi |
| Entamoeba coli | Plasmodium falciparum |
| Entamoeba gingivalis | Plasmodium vivax |
| Entamoeba histolytica | Prototheca wickerhamii |
| Euglena gracilis | Tetracystis disociata |
| Giardia intestinalis | Tetrahymena borealis |
| Giardia lamblia | Tetrahymena thermophila |
| Haematococcus lacustris | Trichomonas gallinae |
| Hartmannella limax | Trichomonas vaginalis |
| Herpetomonas mariadeanei | Tritrichomonas foetus |
| Leishmania braziliensis | Trypanosoma brucei |
| Leishmania donovani | Trypanosoma cruzi |

We claim:

1. A biocidal, aqueous, composition for killing bacteria, spores, fungi, and viruses on nonabsorbent surface comprising:
   a) two heterocyclic quaternary ammonium compounds, each in the amount of from about 0.05 to 3 percent by weight;
   b) one aliphatic dialdehyde having from 2 to 6 carbon atoms in the amount of from about 0.5 to about 7 percent by weight; and
   c) at least one aliphatic hydroxyl compound having from 1 to 8 carbon atoms in the amount from 0.1 to about 3 percent by weight; all weight percents being in the final use dilution.

2. The biocidal composition of claim 1, wherein the weight percent of the aliphatic dialdehyde in the final use dilution is in the amount of from about 2.6 to about 5 weight percent.

3. The biocidal composition of claim 1, further comprising a chelating agent in the amount of zero to about 0.025 weight percent of the final use dilution.

4. The biocidal composition of claim 3, wherein the chelating agent is tetrasodium ethylenediamine tetraacetate.

5. The biocidal composition of claim 1 wherein the dialdehyde is 1,5-pentanedial (glutaraldehyde) comprising from 2.6 to 3.2 weight percent of the final use dilution.

6. The biocidal composition of claim 1, wherein the heterocyclic quaternary ammonium compound contains an aromatic moiety.

7. The biocidal composition of claim 1, wherein one of the heterocyclic quaternary ammonium compounds is n-hexylpyridinium halide.

8. The biocidal composition of claim 1, wherein both of the heterocyclic quaternary ammonium compounds are the same.

9. The biocidal composition of claim 1, wherein the aliphatic hydroxyl compound is selected from the group consisting of isopropyl alcohol, propylene glycol, and their mixtures.

10. The biocidal composition of claim 1, further comprising a soluble, inorganic, nitrite salt.

11. The biocidal composition of claim 1, wherein all the all the quaternary ammonium compounds are halide salts.

12. A method for sterilizing a nonabsorbent surface comprising the steps of contacting said surface with an effective sterilizing amount of an aqueous composition comprising:
  a) two heterocyclic quaternary ammonium compounds, each in the amount of from about 0.05 to 3 percent by weight;
  b) one aliphatic dialdehyde having from 2 to 6 carbon atoms in the amount of from about 0.5 to about 7 percent by weight; and
  c) at least one aliphatic hydroxyl compound having from one to eight carbon atoms in the amount from about 0.1 to about 3 percent by weight; all weight percents being in the final use dilution; and killing on said surface bacteria, spores, fungi, and viruses.

* * * * *